United States Patent [19]
Innerarity et al.

[11] Patent Number: 5,866,333
[45] Date of Patent: Feb. 2, 1999

[54] SCREENING METHODS TO DETECT MRNA TARGETS OF EDITING ENZYMES

[75] Inventors: Thomas L. Innerarity, Lafayette; Xiaobing Qian; Shinya Yamanaka, both of San Francisco, all of Calif.

[73] Assignee: Regents of the University of California, Oakland, Calif.

[21] Appl. No.: 609,230

[22] Filed: Mar. 1, 1996

[51] Int. Cl.⁶ .............................. C12Q 1/68; C12P 19/34; C07H 21/04

[52] U.S. Cl. .......................... 435/6; 435/91.2; 536/24.33; 935/77; 935/78

[58] Field of Search ........................... 435/6, 91.2, 91.1; 536/243, 24.33

[56] References Cited

U.S. PATENT DOCUMENTS

| | | | |
|---|---|---|---|
| 5,389,514 | 2/1995 | Taylor | 435/6 |
| 5,434,058 | 7/1995 | Davidson | 435/69.1 |
| 5,550,034 | 8/1996 | Teng et al. | 435/69.1 |
| 5,643,778 | 7/1997 | Nishikura | 435/227 |

FOREIGN PATENT DOCUMENTS

WO96/30504  10/1996  WIPO ............................. C12N 15/00

OTHER PUBLICATIONS

Davies et al. (1989) J. Biol. Chem. 264:13395–13398.

Navaratnam et al. (1991) Nucl. Acids Res. 19:1741–1744.

Davidson et al. (1988) J. Biol. Chem. 263:13482–13485.

Shaugnhessy, J.D. et al., "The mammalian homolog of the p82 subunit of wheat eIF–(iso)4F: cDNA cloning, expression analysis, and chromosomal localization," Genebank Accession No. U63323 (1996).

Backus, et. al. "Only cytidines 5' of the apolipoprotein B mRNA mooring sequence are edited", *Biochem. Biophys. Acta.* 1217: 65–73 (1994).

Backus, et. al. "Specific 3' sequences flanking a minimal apolipoprotein B (apoB) MRNA editing 'cassette' are critical for efficient editing in vitro", *Biochem. Biophys. Acta.* 1219: 1–14 (1994).

Campfield, et. al. "Recombinant Mouse OB Protein: Evidence for a Peripheral Signal Linking Adiposity and Central Neural Networks", *Science* 269: 546–549 (1995).

Chua, et. al. "Phenotypes of Muose diabetes and Rat fatty Due to Mutations in the OB (Letpin) Receptor", *Science* 271: 994–996 (1996).

Davidson, et. al. "Proposed nomenclature for the catalytic subunit of the mammalian apolipoprotein B mRNA editing enzyme: APOBEC–1", *RNA* 1:3 (1995).

Driscoll, et. al. "Induction of RNA Editing at Heterologous Sites by Sequences in Apolipoprotein B mRNA", *Mol. Cell. Biol.* 13: 7288–7294 (1993).

Friedman, et. al. "Molecular Mapping of the Mouse ob Mutation", *Genomics* 11: 1054–1062 (1991).

Hadjiagapiou, et. al. "Molecular cloning of a human small intestinal apolipoprotein B mRNA editing protein", *Nucleic Acids Res.* 22: 1874–1879 (1994).

Halaas, et. al. "Weight–Reducing Effects of the Plasma Protein Encoded by the obese Gene", *Science* 269: 543–546 (1995).

Lau, et. al. "Dimeric structure of a human apolipoprotein B mRNA editing protein and cloning and chromosomal localization of its gene", *Proc. Natl. Acad. Sci. U.S.A.* 91: 8522–8526 (1994).

(List continued on next page.)

*Primary Examiner*—Stephanie W. Zitomer
*Attorney, Agent, or Firm*—Townsend and Townsend and Crew LLP; Renee A. Fitts

[57] ABSTRACT

The expression of APOBEC-1 in the liver of transgenic mice can cause liver dysplasia and liver tumors, and the expression of human APOBEC-1 in the intestine, stomach, or brain can cause obesity. Promiscuous editing of other mRNAs is correlated to these phenotypic changes. The instant invention discloses novel techniques for detecting aberrantly edited mRNAs, and hence, genes responsible for non-wild type phenotypes.

9 Claims, 6 Drawing Sheets

OTHER PUBLICATIONS

Liang & Pardee "Differential Display of Eukaryotic Messenger RNA by Means of the Polymerase Chain Reaction", *Science* 257: 967–971 (1992).

Nakamuta, et. al. "Alternative mRNA Splicing and Differential Promoter Utilization Determine Tissue–specific Expression of the Apolipoprotein B mRNA–editing Protein (Apobec1) Gene in Mice", *J. Biol. Chem.* 270: 13042–13056 (1995).

Pelleymounter, et. al. "Effects of the obese Gene Product on Body Weight Regulation in ob/ob Mice", *Science* 269: 540–543 (1995).

Reeves, et. al. "General Method for PCR Amplification and Direct Sequencing of mRNA Differential Display Products", *Biotechniques* 18: 18–20 (1995).

Shah, et. al. "Sequence Requirements for the Editing of Apolipoprotein B mRNA", *J. Biol. Chem.* 266: 16301–16304 (1991).

Tartaglia, et. al. "Identification and Expression Cloning of a Leptin Receptor, OB–R", *Cell* 83: 1263 (1995).

Teng, et. al. "Molecular Cloning of an Apolipoprotein B Messenger RNA Editing Protein", *Science* 260: 1816–1819 (1993).

Wang & Feuerstein "Direct Sequencing of DNA Isolated from mRNA Differential Display", *Biotechniques* 18: 448–452 (1995).

Yamanaka, et. al. "Cloning and Mutagenesis of the Rabbit ApoB mRNA Editing Protein", *J. Biol. Chem.* 269: 21725–21734 (1994).

Yamanaka, et. al. "Apolipoprotein B mRNA–editing protein induces hepatocellular carcinoma and dysplasia in transgenic animals", *Proc. Natl. Acad. Sci. U.S.A.* 92: 8483–8487 (1995).

Zhang, et. al. "Positional cloning of the mouse obese gene and its human homologue", *Nature* 372: 425–432 (1994).

```
    ↓                              ↓  ↓                ↓
    CCTATTATAGTATTGAAATTAAGTCTACTTAATTTATC

↓          ↓                        ↓           ↓
    AAGTCATGTTCATGCCCTGATTTTATATACTTGTATCT
```

```
cggcgggtaccaggtggcggctgcagcagctactcctctgagctgagact     50
ttcaagccggccgcgtctccttcctccccttccctcccccttttttgtt    100
ttccgttccccttcccctccttccccgtcccgacgaccggatccaga     150
ggaggcagctgcggtggcagctgctgagttctcggtgaaggcttttcatt   200
tctaccatcccctccctccccacccatccattaatattattcttttga     250
agattcttcgttgtcaagccgccaaaGTGGAGAGTGCGATTGCAGAAGGG   300
                          V  E  S  A  I  A  E  G      8
GGTGCTTCTCGTTTCAGTGCTTCTTCGGGCGGAGGAGGAAGTAGGGGTGC   350
 G  A  S  R  F  S  A  S  S  G  G  G  S  R  G  A      25
ACCTCAGCACTATCCCAAGACTGCTGGCAACAGCGAGTTCCTGGGGAAAA   400
  P  Q  H  Y  P  K  T  A  G  N  S  E  F  L  G  K  T  42
CCCCAGGGCAAAACGCTCAGAAATGGATTCCTGCACGAAGCACTAGACGA   450
  P  G  Q  N  A  Q  K  W  I  P  A  R  S  T  R  R     58
GATGACAACTCCGCAGCAAACAACTCCGCAAATGAAAAGAACGACATGA    500
 D  D  N  S  A  A  N  N  S  A  N  E  K  E  R  H  D   75
TGCAATCTTCAGGAAAGTAAGAGGCATACTAAATAAGCTTACTCCTGAAA   550
  A  I  F  R  K  V  R  G  I  L  N  K  L  T  P  E  K 92
AGTTTGACAAGCTATGCCTTGAGCTCCTCAATGTGGGTGTAGAGTCTAAA   600
  F  D  K  L  C  L  E  L  L  N  V  G  V  E  S  K    108
CTCATCCTTAAAGGGGTCATACTGCTGATTGTGGACAAAGCCCTAGAGGA   650
 L  I  L  K  G  V  I  L  L  I  V  D  K  A  L  E  E  125
GCCAAAGTATAGCTCACTGTATGCTCAGCTATGTCTGCGATTGGCAGAAG   700
  P  K  Y  S  S  L  Y  A  Q  L  C  L  R  L  A  E  D 142
ATGCACCAAACTTTGATGGCCCAGCAGCAGAGGGTCAACCAGGACAGAAG   750
  A  P  N  F  D  G  P  A  A  E  G  Q  P  G  Q  K    158
CAAAGCACAACATTCAGACGCCTCTTGATTTCCAAATTGCAAGATGAATT   800
 Q  S  T  T  F  R  R  L  L  I  S  K  L  Q  D  E  F  175
TGAAAACCGAACCAGAAATGTTGATGTCTATGATAAGCGTGAAAATCCCC   850
  E  N  R  T  R  N  V  D  V  Y  D  K  R  E  N  P  L 192
TCCTTCCTGAGCACGAGGAACAGAGAGCCATTGCTAAGATCAAGATGTTG   900
 L  P  E  E  E  E  Q  R  A  I  A  K  I  K  M  L     208
GGGAACATCAAATTCATTGGAGAACTTGGCAAGCTTGATCTTATTCATGA   950
 G  N  I  K  F  I  G  E  L  G  K  L  D  L  I  H  E  225
ATCTATCCTTCATAAGTGCATCAAAACACTTTTGGAAAAGAAGAAGAGAG  1000
  S  I  L  H  K  C  I  K  T  L  L  E  K  K  K  R  V 242
TCCAACTCCAAGATATGGGAGAGGATTTGGAGTGCCTCTGTCAGATAATG  1050
  Q  L  Q  D  M  G  E  D  L  E  C  L  C  Q  I  M    258
AGGACAGTGGGACCTCGATTAGACCATGAACGAGCCAAGTCCTTAATGGA  1100
 R  T  V  G  P  R  L  D  H  E  R  A  K  S  L  M  D  275
TCAGTACTTTGCCAGAATGTGTTCCTTAATGTTAAGTAAGGAATTGCCAG  1150
  Q  Y  F  A  R  M  C  S  L  M  L  S  K  E  L  P  A 292
CCAGGATTCGTTTCCTACTGCAGGATACTGTAGAGTTGCGAGAGCACCAT  1200
   R  I  R  F  L  L  Q  D  T  V  E  L  R  E  H  H   308
```

FIG. 5A.

```
TGGGTTCCTCGCAAGGCTTTTCTTGACAATGGACCAAAGACGATCAATCA 1250
 W  V  P  R  K  A  F  L  D  N  G  P  K  T  I  N  Q    325
AATCCGTCAAGATGCAGTAAAAGATCTAGGAGTGTTTATTCCTGCTCCTA 1300
  I  R  Q  D  A  V  K  D  L  G  V  F  I  P  A  P  M  342
TGGCTCAAGGGAGAAGTGACTTCTTCCTGGAGGGACCGTTCATGCCGCCA 1350
   A  Q  G  R  S  D  F  F  L  E  G  P  F  M  P  P    358
AGGATGAAAATGGATAGGGACCCACTTGGGGGACTTGCTGATATGTTTGG 1400
 R  M  K  M  D  R  D  P  L  G  G  L  A  D  M  F  G   375
ACAAATGCCAGGTAGTGGAATTGGTACTGGTCCAGGAGTTATCCAGGATA 1450
 Q  M  P  G  S  G  I  G  T  G  P  G  V  I  Q  D  R   392
GATTTTCACCCACAATGGGACGTCATCGTTCAAATCAGCTCTTCAATGGC 1500
  F  S  P  T  M  G  R  H  R  S  N  Q  L  F  N  G    408
CATGGGGGGCACATCATGCCTCCCACGCAATCGCAGTTTGGAGAGATGGG 1550
  H  G  G  H  I  M  P  P  T  Q  S  Q  F  G  E  M  G  425
GGGCAAGTTTATGAAAAGCCAGGGGCTAAGCCAGCTCTACCATAACCAGA 1600
   G  K  F  M  K  S  Q  G  L  S  Q  L  Y  H  N  Q  S 442
GTCAGGGACTCTTATCCCAGCTGCAAGGACAGTCGAAGGATATGCCACCT 1650
    Q  G  L  L  S  Q  L  Q  G  Q  S  K  D  M  P  P   458
CGGTTTTCTAAGAAAGGACAGCTTAATGCAGATGAGATTAGTTTGAGGCC 1700
 R  F  S  K  K  G  Q  L  N  A  D  E  I  S  L  R  P   475
TGCTCAGTCGTTTCTAATGAATAAAAATCAGGTGCCAAAGCTTCAGCCCC 1750
  A  Q  S  F  L  M  N  K  N  Q  V  P  K  L  Q  P  Q  492
AGATAACTATGATTCCTCCCAGTGCACAGCCACCACGCACTCAAACACCG 1800
   I  T  M  I  P  P  S  A  Q  P  P  R  T  Q  T  P    508
CCTCTGGGACAGACACCTCAACTTGGTCTCAAAACTAATCCACCACTTAT 1850
 P  L  G  Q  T  P  Q  L  G  L  K  T  N  P  P  L  I   525
CCAGGAAAAGCCTGCCAAGACTAGCAAAAAGCCACCACCATCAAAGGAAG 1900
  Q  E  K  P  A  K  T  S  K  K  P  P  P  S  K  E  E  542
AACTACTTAAACTGACCGAAGCCGTTGTGACTGACTATCTGAACAGTGGA 1950
    L  L  K  L  T  E  A  V  V  T  D  Y  L  N  S  G   558
AATGCCAACGACGCTGTCAGTGGTGTGAGAGAAATGAGAGCTCCAAAACA 2000
 N  A  N  D  A  V  S  G  V  R  E  M  R  A  P  K  H   575
CTTTCTTCCTGAGATGCTAAGCAAAGTGATCATCCTGTCACTTGATAGAA 2050
  F  L  P  E  M  L  S  K  V  I  I  L  S  L  D  R  S  592
GCGATGAAGATAAAGAAAAGCAAGCTCTTTAATCAGTTTACTCAAACAG 2100
   D  E  D  K  E  K  A  S  S  L  I  S  L  L  K  Q    608
GAAGGGATAGCCACAAGTGACAACTTCATGCAGGCTTTCCTGAATGTATT 2150
 E  G  I  A  T  S  D  N  F  M  Q  A  F  L  N  V  L   625
GGAGCAGTGCCCCAAACTGGAGGTTGACATCCCCTTGGTGAAATCTTACT 2200
  E  Q  C  P  K  L  E  V  D  I  P  L  V  K  S  Y  L  642
TGGCACAGTTTGCAGCTCGTGCTATAATTTCAGAGTTGGTGAGCATTTCC 2250
   A  Q  F  A  A  R  A  I  I  S  E  L  V  S  I  S    658
GAACTAGCTCAACCACTGGAGAGTGGCACCCACTTCCCTCTCTTCTTACT 2300
 E  L  A  Q  P  L  E  S  G  T  H  F  P  L  F  L  L   675
```

*FIG. 5B.*

```
TTGTCTTCAACAATTAGCTAAATTGCAAGACCGAGAGTGGTTAACCGAAC 2350
 C  L  Q  Q  L  A  K  L  D  R  E  W  L  T  E  L    692
TTTTTCAACAAAGCAAGGTCAATATGCAGAAATGCTGCCAGAAATTGAT 2400
   F  Q  Q  S  K  V  N  M  Q  K  M  L  P  E  I  D  708
CAGAATAAGGATCGAATGTTGGAGATTTTGGAAGGAAAGGGACTGAGTTT 2450
 Q  N  K  D  R  M  L  E  I  L  E  G  K  G  L  S  F  725
CTTATTCCCACTCCTTAAATTGGAGAAGGAACTATTGAAGCAAATTAAGC 2500
  L  F  P  L  L  K  L  E  K  E  L  L  K  Q  I  K  L  742
TGGATCCATCCCCTCAAACTATATATAAATGGATTAAAGATAACATCTCT 2550
   D  P  S  P  Q  T  I  Y  K  W  I  K  D  N  I  S   758
CCCAAACTTCATGTAGATAAAGGATTCGTGAACATCTTAATGACCAGCTT 2600
  P  K  L  H  V  D  K  G  F  V  N  I  L  M  T  S  F 775
CTTACAGTACATTTCTAGTGAAGTAAGCCCACCCAGCGATGAAACAGATT 2650
  L  Q  Y  I  S  S  E  V  S  P  P  S  D  E  T  D  S 792
CTTCCTCTGCTCCTTCCAAAGAGCAGTTAGAGCAGGAAAAACAGCTGCTG 2700
   S  S  A  P  S  K  E  Q  L  E  Q  E  K  Q  L  L   808
CTCTCTTTTAAGCCAGTGATGCAGAAATTTCTTCATGATCATGTGGATCT 2750
 L  S  F  K  P  V  M  Q  K  F  L  H  D  H  V  D  L  825
ACAGGTCAGTGCCCTGTATGCTTTTCAGGTGCACTGTTACAACAGCAGCT 2800
  Q  V  S  A  L  Y  A  F  Q  V  H  C  Y  N  S  S  F 842
TCCCAAAAGGCATGTTACTTCGATTTTTTGTTCACTTCTATGACATGGAA 2850
   P  K  G  M  L  L  R  F  F  V  H  F  Y  D  M  E   858
ATTATTGAAGAGGAAGCTTTCTTAGCTTGGAAGGAAGACATAACTCAAGA 2900
 I  I  E  E  E  A  F  L  A  W  K  E  D  I  T  Q  E  875
GTTTCCAGGAAAAGGCAAGGCTTTGTTCCAGGTGAATCAGTGGCTAACCT 2950
  F  P  G  K  G  K  A  L  F  Q  V  N  Q  W  L  T  W 890
GGCTAGAAACTGCTGAAGAAGAAGAATCAGAGGAAGAAGCTGACtaaaga 3000
   L  E  T  A  E  E  E  E  S  E  E  E  A  D
accagccaaagccttaaattgtgcaaaacatactgttgctatgatgtaac 3050
tgcatttgacctaaccactgcgaaaattcattccgctgtaacgttttttc 3100
acaatatttaaagcagaagcacgtcagtaaggttccttctgcataaggt 3150
ttttgtagtgtgatgtcttaatcatagtctaccatcaaatactttaggag 3200
tatccttaatgtttagatagaatattagcagcatgcaataattacatcct 3250
aagttctcaagcagaagcagtctattgcaaggaccttctttgctgccagt 3300
taccataggctgttttaagttagaaaactgaatagcaacactgaatactg 3350
tagaaatgcactttgctcagtaatacttgagttgttgcaatatttgatta 3400
tccatttggttgttacagaaaaattcttaactgtaattgatggttgttgc 3450
cgtaatagtatattgcctgtatttctacctctagtaatgggctttatgtg 3500
ctagattttaaaatccttgagcctgggcaagtgcacaagtcttttttaaaa 3550
gaaacatggtttacttgcaccaaactgatcagtttgagagatcattaatg 3600
cccttgaagtggttttttgtgggtgtgaaacaaatggtgagaatttgaatt 3650
ggtccctcttattatagtattgaaattaagtctacttaatttatcaagtc 3700
atgttcatgccctgattttatatacttgtatctatcaataaacattgtga 3750
a                                                  3751
```

FIG. 5C.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:1:

U G A U C A N U A U  A                        1 1

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

G A T C A T A G C C                      1 0

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:3:

C N N N N U G A U C  A N U A U A              1 6

( 2 ) INFORMATION FOR SEQ ID NO:4:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:4:

ANNNNACTAG TNATAT                          1 6

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:5:

UNNNNUGAUC ANUAUA                          1 6

( 2 ) INFORMATION FOR SEQ ID NO:6:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CCTATTATAG TATTGAAATT AAGTCTACTT AATTTATC          3 8

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

AAGTCATGTT CATGCCCTGA TTTTATATAC TTGTATCT          3 8

( 2 ) INFORMATION FOR SEQ ID NO:8:

( i ) SEQUENCE CHARACTERISTICS:
        ( A ) LENGTH: 3751 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 277..2994

( x i ) SEQUENCE DESCRIPTION: SEQ ID NO:8:

CGGCGGGTAC CAGGTGGCGG CTGCAGCAGC TACTCCTCTG AGCTGAGACT TTCAAGCCGG      60

CCGCGTCTCC TTCCTCCCCC TTCCCTCCCC CTTTTTTGTT CTCCGTTCCC CTTCCCCCTC      120

CCTTCCCCGT CCCCGACGAC CGGATCCAGA GGAGGCAGCT GCGGTGGCAG CTGCTGAGTT      180

```
CTCGGTGAAG GCTTTTCATT TCTACCATCC CCTCCCCTCC CCACCCCATC CATTAATATT         240

ATTCTTTTGA AGATTCTTCG TTGTCAAGCC GCCAAA GTC GAG AGT GCG ATT GCA          294
                                         Val Glu Ser Ala Ile Ala
                                          1               5

GAA GGG GGT GCT TCT CGT TTC AGT GCT TCT TCG GGC GGA GGA GGA AGT          342
Glu Gly Gly Ala Ser Arg Phe Ser Ala Ser Ser Gly Gly Gly Gly Ser
            10              15                      20

AGG GGT GCA CCT CAG CAC TAT CCC AAG ACT GCT GGC AAC AGC GAG TTC          390
Arg Gly Ala Pro Gln His Tyr Pro Lys Thr Ala Gly Asn Ser Glu Phe
        25              30                      35

CTG GGG AAA ACC CCA GGG CAA AAC GCT CAG AAA TGG ATT CCT GCA CGA          438
Leu Gly Lys Thr Pro Gly Gln Asn Ala Gln Lys Trp Ile Pro Ala Arg
    40              45                      50

AGC ACT AGA CGA GAT GAC AAC TCC GCA GCA AAC AAC TCC GCA AAT GAA          486
Ser Thr Arg Arg Asp Asp Asn Ser Ala Ala Asn Asn Ser Ala Asn Glu
 55              60                      65                      70

AAA GAA CGA CAT GAT GCA ATC TTC AGG AAA GTA AGA GGC ATA CTA AAT          534
Lys Glu Arg His Asp Ala Ile Phe Arg Lys Val Arg Gly Ile Leu Asn
                     75              80                      85

AAG CTT ACT CCT GAA AAG TTT GAC AAG CTA TGC CTT CAG CTC CTC AAT          582
Lys Leu Thr Pro Glu Lys Phe Asp Lys Leu Cys Leu Gln Leu Leu Asn
             90              95                     100

GTG GGT GTA GAG TCT AAA CTC ATC CTT AAA GGG GTC ATA CTG CTG ATT          630
Val Gly Val Glu Ser Lys Leu Ile Leu Lys Gly Val Ile Leu Leu Ile
        105             110                     115

GTG GAC AAA GCC CTA GAG GAG CCA AAG TAT AGC TCA CTG TAT GCT CAG          678
Val Asp Lys Ala Leu Glu Glu Pro Lys Tyr Ser Ser Leu Tyr Ala Gln
    120             125                     130

CTA TGT CTG CGA TTG GCA GAA GAT GCA CCA AAC TTT GAT GGC CCA GCA          726
Leu Cys Leu Arg Leu Ala Glu Asp Ala Pro Asn Phe Asp Gly Pro Ala
135             140                     145                     150

GCA GAG GGT CAA CCA GGA CAG AAG CAA AGC ACA ACA TTC AGA CGC CTC          774
Ala Glu Gly Gln Pro Gly Gln Lys Gln Ser Thr Thr Phe Arg Arg Leu
            155                     160                     165

TTG ATT TCC AAA TTG CAA GAT GAA TTT GAA AAC CGA ACC AGA AAT GTT          822
Leu Ile Ser Lys Leu Gln Asp Glu Phe Glu Asn Arg Thr Arg Asn Val
            170                     175                     180

GAT GTC TAT GAT AAG CGT GAA AAT CCC CTC CTT CCT GAG CAC GAG GAA          870
Asp Val Tyr Asp Lys Arg Glu Asn Pro Leu Leu Pro Glu His Glu Glu
        185                     190                     195

CAG AGA GCC ATT GCT AAG ATC AAG ATG TTG GGG AAC ATC AAA TTC ATT          918
Gln Arg Ala Ile Ala Lys Ile Lys Met Leu Gly Asn Ile Lys Phe Ile
        200                     205                     210

GGA GAA CTT GGC AAG CTT GAT CTT ATT CAT GAA TCT ATC CTT CAT AAG          966
Gly Glu Leu Gly Lys Leu Asp Leu Ile His Glu Ser Ile Leu His Lys
215                     220                     225                 230

TGC ATC AAA ACA CTT TTG GAA AAG AAG AAG AGA GTC CAA CTC CAA GAT         1014
Cys Ile Lys Thr Leu Leu Glu Lys Lys Lys Arg Val Gln Leu Gln Asp
            235                     240                     245

ATG GGA GAG GAT TTG GAG TGC CTC TGT CAG ATA ATG AGG ACA GTG GGA         1062
Met Gly Glu Asp Leu Glu Cys Leu Cys Gln Ile Met Arg Thr Val Gly
            250                     255                     260

CCT CGA TTA GAC CAT GAA CGA GCC AAG TCC TTA ATG GAT CAG TAC TTT         1110
Pro Arg Leu Asp His Glu Arg Ala Lys Ser Leu Met Asp Gln Tyr Phe
        265                     270                     275

GCC AGA ATG TGT TCC TTA ATG TTA AGT AAG GAA TTG CCA GCC AGG ATT         1158
Ala Arg Met Cys Ser Leu Met Leu Ser Lys Glu Leu Pro Ala Arg Ile
        280                     285                     290

CGT TTC CTA CTG CAG GAT ACT GTA GAG TTG CGA GAG CAC CAT TGG GTT         1206
Arg Phe Leu Leu Gln Asp Thr Val Glu Leu Arg Glu His His Trp Val
```

-continued

```
                  295                           300                           305                           310
CCT  CGC  AAG  GCT  TTT  CTT  GAC  AAT  GGA  CCA  AAG  ACG  ATC  AAT  CAA  ATC                              1254
Pro  Arg  Lys  Ala  Phe  Leu  Asp  Asn  Gly  Pro  Lys  Thr  Ile  Asn  Gln  Ile
                    315                      320                           325

CGT  CAA  GAT  GCA  GTA  AAA  GAT  CTA  GGA  GTG  TTT  ATT  CCT  GCT  CCT  ATG                              1302
Arg  Gln  Asp  Ala  Val  Lys  Asp  Leu  Gly  Val  Phe  Ile  Pro  Ala  Pro  Met
               330                      335                           340

GCT  CAA  GGG  AGA  AGT  GAC  TTC  TTC  CTG  GAG  GGA  CCG  TTC  ATG  CCG  CCA                              1350
Ala  Gln  Gly  Arg  Ser  Asp  Phe  Phe  Leu  Glu  Gly  Pro  Phe  Met  Pro  Pro
               345                      350                           355

AGG  ATG  AAA  ATG  GAT  AGG  GAC  CCA  CTT  GGG  GGA  CTT  CGT  GAT  ATG  TTT                              1398
Arg  Met  Lys  Met  Asp  Arg  Asp  Pro  Leu  Gly  Gly  Leu  Arg  Asp  Met  Phe
          360                      365                           370

GGA  CAA  ATG  CCA  GGT  AGT  GGA  ATT  GGT  ACT  GGT  CCA  GGA  GTT  ATC  CAG                              1446
Gly  Gln  Met  Pro  Gly  Ser  Gly  Ile  Gly  Thr  Gly  Pro  Gly  Val  Ile  Gln
375                      380                           385                      390

GAT  ACA  TTT  TCA  CCC  ACA  ATG  GGA  CGT  CAT  CGT  TCA  AAT  CAG  CTC  TTC                              1494
Asp  Thr  Phe  Ser  Pro  Thr  Met  Gly  Arg  His  Arg  Ser  Asn  Gln  Leu  Phe
                              395                      400                           405

AAT  GGC  CAT  GGG  GGG  CAC  ATC  ATG  CCT  CCC  ACG  CAA  TCG  CAG  TTT  GGA                              1542
Asn  Gly  His  Gly  Gly  His  Ile  Met  Pro  Pro  Thr  Gln  Ser  Gln  Phe  Gly
               410                           415                      420

GAG  ATG  GGG  GGC  AAG  TTT  ATG  AAA  AGC  CAG  GGG  CTA  AGC  CAG  CTC  TAC                              1590
Glu  Met  Gly  Gly  Lys  Phe  Met  Lys  Ser  Gln  Gly  Leu  Ser  Gln  Leu  Tyr
          425                      430                           435

CAT  AAC  CAG  AGT  CAG  GGA  CTC  TTA  TCC  CAG  CTG  CAA  GGA  CAG  TCG  AAG                              1638
His  Asn  Gln  Ser  Gln  Gly  Leu  Leu  Ser  Gln  Leu  Gln  Gly  Gln  Ser  Lys
          440                      445                           450

GAT  ATG  CCA  CCT  CGG  TTT  TCT  AAG  AAA  GGA  CAG  CTT  AAT  GCA  GAT  GAG                              1686
Asp  Met  Pro  Pro  Arg  Phe  Ser  Lys  Lys  Gly  Gln  Leu  Asn  Ala  Asp  Glu
455                      460                           465                      470

ATT  AGT  TTG  AGG  CCT  GCT  CAG  TCG  TTT  CTA  ATG  AAT  AAA  AAT  CAG  GTG                              1734
Ile  Ser  Leu  Arg  Pro  Ala  Gln  Ser  Phe  Leu  Met  Asn  Lys  Asn  Gln  Val
                    475                      480                           485

CCA  AAG  CTT  CAG  CCC  CAG  ATA  ACT  ATG  ATT  CCT  CCC  AGT  GCA  CAG  CCA                              1782
Pro  Lys  Leu  Gln  Pro  Gln  Ile  Thr  Met  Ile  Pro  Pro  Ser  Ala  Gln  Pro
               490                      495                           500

CCA  CGC  ACT  CAA  ACA  CCG  CCT  CTG  GGA  CAG  ACA  CCT  CAA  CTT  GGT  CTC                              1830
Pro  Arg  Thr  Gln  Thr  Pro  Pro  Leu  Gly  Gln  Thr  Pro  Gln  Leu  Gly  Leu
          505                      510                           515

AAA  ACT  AAT  CCA  CCA  CTT  ATC  CAG  GAA  AAG  CCT  GCC  AAG  ACT  AGC  AAA                              1878
Lys  Thr  Asn  Pro  Pro  Leu  Ile  Gln  Glu  Lys  Pro  Ala  Lys  Thr  Ser  Lys
520                      525                           530

AAG  CAA  CCA  CCA  TCA  AAG  GAA  GAA  CTA  CTT  AAA  CTG  ACC  GAA  GCC  GTT                              1926
Lys  Gln  Pro  Pro  Ser  Lys  Glu  Glu  Leu  Leu  Lys  Leu  Thr  Glu  Ala  Val
535                      540                           545                      550

GTG  ACT  GAC  TAT  CTG  AAC  AGT  GGA  AAT  GCC  AAC  GAG  GCT  GTC  AGT  GGT                              1974
Val  Thr  Asp  Tyr  Leu  Asn  Ser  Gly  Asn  Ala  Asn  Glu  Ala  Val  Ser  Gly
                    555                      560                           565

GTG  AGA  GAA  ATG  AGA  GCT  CCA  AAA  CAC  TTT  CTT  CCT  GAG  ATG  CTA  AGC                              2022
Val  Arg  Glu  Met  Arg  Ala  Pro  Lys  His  Phe  Leu  Pro  Glu  Met  Leu  Ser
               570                      575                           580

AAA  GTG  ATC  ATC  CTG  TCA  CTT  GAT  AGA  AGC  GAT  GAA  GAT  AAA  GAA  AAA                              2070
Lys  Val  Ile  Ile  Leu  Ser  Leu  Asp  Arg  Ser  Asp  Glu  Asp  Lys  Glu  Lys
               585                      590                           595

GCA  AGC  TCT  TTA  ATC  AGT  TTA  CTC  AAA  CAG  GAA  GCG  ATA  GCC  ACA  AGT                              2118
Ala  Ser  Ser  Leu  Ile  Ser  Leu  Leu  Lys  Gln  Glu  Ala  Ile  Ala  Thr  Ser
          600                      605                           610

GAC  AAC  TTC  ATG  CAG  GCT  TTC  CTG  AAT  GTA  TTG  GAG  CAG  TGC  CCC  AAA                              2166
Asp  Asn  Phe  Met  Gln  Ala  Phe  Leu  Asn  Val  Leu  Glu  Gln  Cys  Pro  Lys
```

```
615                         620                         625                         630
CTG GAG GTT GAC ATC CCC TTG GTG AAA TCT TAC TTG GCA CAG TTT GCA                         2214
Leu Glu Val Asp Ile Pro Leu Val Lys Ser Tyr Leu Ala Gln Phe Ala
            635                         640                         645

GCT CGT GCT ATA ATT TCA GAG TTG GTG AGC ATT TCC GAA CTA GCT CAA                         2262
Ala Arg Ala Ile Ile Ser Glu Leu Val Ser Ile Ser Glu Leu Ala Gln
            650                         655                         660

CCA CTG GAG AGT GGC ACC CAC TTC CCT CTC TTC TTA CTT TGT CTT CAA                         2310
Pro Leu Glu Ser Gly Thr His Phe Pro Leu Phe Leu Leu Cys Leu Gln
            665                         670                         675

CAA TTA GCT AAA TTG CAA GAC CGA GAG TGG TTA ACC GAA CTT TTT CAA                         2358
Gln Leu Ala Lys Leu Gln Asp Arg Glu Trp Leu Thr Glu Leu Phe Gln
            680                         685                         690

CAA AGC AAG GTC AAT ATG CAG AAA ATG CTG CCA GAA ATT GAT CAG AAT                         2406
Gln Ser Lys Val Asn Met Gln Lys Met Leu Pro Glu Ile Asp Gln Asn
695                         700                         705                         710

AAG GAT CGA ATG TTG GAG ATT TTG GAA GGA AAG GGA CTG AGT TTC TTA                         2454
Lys Asp Arg Met Leu Glu Ile Leu Glu Gly Lys Gly Leu Ser Phe Leu
            715                         720                         725

TTC CCA CTC CTT AAA TTG GAG AAG GAA CTA TTG AAG CAA ATT AAG CTG                         2502
Phe Pro Leu Leu Lys Leu Glu Lys Glu Leu Leu Lys Gln Ile Lys Leu
            730                         735                         740

GAT CCA TCC CCT CAA ACT ATA TAT AAA TGG ATT AAA GAT AAC ATC TCT                         2550
Asp Pro Ser Pro Gln Thr Ile Tyr Lys Trp Ile Lys Asp Asn Ile Ser
            745                         750                         755

CCC AAA CTT CAT GTA GAT AAA GGA TTC GTG AAC ATC TTA ATG ACC AGC                         2598
Pro Lys Leu His Val Asp Lys Gly Phe Val Asn Ile Leu Met Thr Ser
            760                         765                         770

TTC TTA CAG TAC ATT TCT AGT GAA GTA AGC CCA CCC AGC GAT GAA ACA                         2646
Phe Leu Gln Tyr Ile Ser Ser Glu Val Ser Pro Pro Ser Asp Glu Thr
775                         780                         785                         790

GAT TCT TCC TCT GCT CCT TCC AAA GAG CAG TTA GAG CAG GAA AAA CAG                         2694
Asp Ser Ser Ser Ala Pro Ser Lys Glu Gln Leu Glu Gln Glu Lys Gln
            795                         800                         805

CTG CTG CTC TCT TTT AAG CCA GTG ATG CAG AAA TTT CTT CAT GAT CAT                         2742
Leu Leu Leu Ser Phe Lys Pro Val Met Gln Lys Phe Leu His Asp His
            810                         815                         820

GTG GAT CTA CAG GTC AGT GCC CTG TAT GCT TTT CAG GTG CAC TGT TAC                         2790
Val Asp Leu Gln Val Ser Ala Leu Tyr Ala Phe Gln Val His Cys Tyr
            825                         830                         835

AAC AGC AGC TTC CCA AAA GGC ATG TTA CTT CGA TTT TTT GTT CAC TTC                         2838
Asn Ser Ser Phe Pro Lys Gly Met Leu Leu Arg Phe Phe Val His Phe
840                         845                         850

TAT GAC ATG GAA ATT ATT GAA GAG GAA GCT TTC TTA GCT TGG AAG GAA                         2886
Tyr Asp Met Glu Ile Ile Glu Glu Glu Ala Phe Leu Ala Trp Lys Glu
855                         860                         865                         870

GAC ATA ACT CAA GAG TTT CCA GGA AAA GGC AAG GCT TTG TTC CAG GTG                         2934
Asp Ile Thr Gln Glu Phe Pro Gly Lys Gly Lys Ala Leu Phe Gln Val
                        875                         880                         885

AAT CAG TGG CTA ACC TGG CTA GAA ACT GCT GAA GAA GAA GAA TCA GAG                         2982
Asn Gln Trp Leu Thr Trp Leu Glu Thr Ala Glu Glu Glu Glu Ser Glu
            890                         895                         900

GAA GAA GCT GAC TAAAGAACCA GCCAAAGCCT TAAATTGTGC AAAACATACT                             3034
Glu Glu Ala Asp
            905

GTTGCTATGA TGTAACTGCA TTTGACCTAA CCACTGCGAA AATTCATTCC GCTGTAACGT                       3094

TTTTTCACAA TATTTAAAGC AGAAGCACGT CAGTAAGGTT TCCTTCTGCA TAAGGTTTTT                       3154

GTAGTGTGAT GTCTTAATCA TAGTCTACCA TCAAATACTT TAGGAGTATC CTTAATGTTT                       3214
```

```
AGATAGAATA  TTAGCAGCAT  GCAATAATTA  CATCCTAAGT  TCTCAAGCAG  AAGCAGTCTA      3274

TTGCAAGGAC  CTTCTTTGCT  GCCAGTTACC  ATAGGCTGTT  TTAAGTTAGA  AAACTGAATA      3334

GCAACACTGA  ATACTGTAGA  AATGCACTTT  GCTCAGTAAT  ACTTGAGTTG  TTGCAATATT      3394

TGATTATCCA  TTTGGTTGTT  ACAGAAAAAT  TCTTAACTGT  AATTGATGGT  TGTTGCCGTA      3454

ATAGTATATT  GCCTGTATTT  CTACCTCTAG  TAATGGGCTT  TATGTGCTAG  ATTTTAAAAT      3514

CCTTGAGCCT  GGGCAAGTGC  ACAAGTCTTT  TTAAAAGAAA  CATGGTTTAC  TTGCACCAAA      3574

CTGATCAGTT  TGAGAGATCA  TTAATGCCCT  TGAAGTGGTT  TTTGTGGGTG  TGAAACAAAT      3634

GGTGAGAATT  TGAATTGGTC  CCTCTTATTA  TAGTATTGAA  ATTAAGTCTA  CTTAATTTAT      3694

CAAGTCATGT  TCATGCCCTG  ATTTTATATA  CTTGTATCTA  TCAATAAACA  TTGTGAA        3751
```

( 2 ) INFORMATION FOR SEQ ID NO:9:

( i ) SEQUENCE CHARACTERISTICS:
        ( A ) LENGTH: 906 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Val  Glu  Ser  Ala  Ile  Ala  Glu  Gly  Gly  Ala  Ser  Arg  Phe  Ser  Ala  Ser
 1              5                   10                  15

Ser  Gly  Gly  Gly  Gly  Ser  Arg  Gly  Ala  Pro  Gln  His  Tyr  Pro  Lys  Thr
             20                   25                  30

Ala  Gly  Asn  Ser  Glu  Phe  Leu  Gly  Lys  Thr  Pro  Gly  Gln  Asn  Ala  Gln
             35                   40                  45

Lys  Trp  Ile  Pro  Ala  Arg  Ser  Thr  Arg  Arg  Asp  Asp  Asn  Ser  Ala  Ala
       50                 55                  60

Asn  Asn  Ser  Ala  Asn  Glu  Lys  Glu  Arg  His  Asp  Ala  Ile  Phe  Arg  Lys
 65                      70                  75                         80

Val  Arg  Gly  Ile  Leu  Asn  Lys  Leu  Thr  Pro  Glu  Lys  Phe  Asp  Lys  Leu
                  85                      90                  95

Cys  Leu  Gln  Leu  Leu  Asn  Val  Gly  Val  Glu  Ser  Lys  Leu  Ile  Leu  Lys
                 100                     105                 110

Gly  Val  Ile  Leu  Leu  Ile  Val  Asp  Lys  Ala  Leu  Glu  Glu  Pro  Lys  Tyr
            115                     120                 125

Ser  Ser  Leu  Tyr  Ala  Gln  Leu  Cys  Leu  Arg  Leu  Ala  Glu  Asp  Ala  Pro
       130                     135                 140

Asn  Phe  Asp  Gly  Pro  Ala  Ala  Glu  Gly  Gln  Pro  Gly  Gln  Lys  Gln  Ser
145                          150                 155                     160

Thr  Thr  Phe  Arg  Arg  Leu  Leu  Ile  Ser  Lys  Leu  Gln  Asp  Glu  Phe  Glu
                 165                     170                 175

Asn  Arg  Thr  Arg  Asn  Val  Asp  Val  Tyr  Asp  Lys  Arg  Glu  Asn  Pro  Leu
            180                     185                 190

Leu  Pro  Glu  His  Glu  Glu  Gln  Arg  Ala  Ile  Ala  Lys  Ile  Lys  Met  Leu
            195                     200                 205

Gly  Asn  Ile  Lys  Phe  Ile  Gly  Glu  Leu  Gly  Lys  Leu  Asp  Leu  Ile  His
       210                     215                 220

Glu  Ser  Ile  Leu  His  Lys  Cys  Ile  Lys  Thr  Leu  Leu  Glu  Lys  Lys  Lys
225                      230                     235                     240

Arg  Val  Gln  Leu  Gln  Asp  Met  Gly  Glu  Asp  Leu  Glu  Cys  Leu  Cys  Gln
                 245                     250                     255

Ile  Met  Arg  Thr  Val  Gly  Pro  Arg  Leu  Asp  His  Glu  Arg  Ala  Lys  Ser
            260                     265                     270
```

| | | | | | | | | | | | | | | |
|---|---|---|---|---|---|---|---|---|---|---|---|---|---|---|
|Leu|Met|Asp|Gln|Tyr|Phe|Ala|Arg|Met|Cys|Ser|Leu|Met|Leu|Ser|Lys|
| | |275| | | |280| | | | |285| | | |
|Glu|Leu|Pro|Ala|Arg|Ile|Arg|Phe|Leu|Leu|Gln|Asp|Thr|Val|Glu|Leu|
| | |290| | | |295| | | | |300| | | |
|Arg|Glu|His|His|Trp|Val|Pro|Arg|Lys|Ala|Phe|Leu|Asp|Asn|Gly|Pro|
|305| | | | |310| | | | |315| | | | |320|
|Lys|Thr|Ile|Asn|Gln|Ile|Arg|Gln|Asp|Ala|Val|Lys|Asp|Leu|Gly|Val|
| | | |325| | | | |330| | | | |335| |
|Phe|Ile|Pro|Ala|Pro|Met|Ala|Gln|Gly|Arg|Ser|Asp|Phe|Phe|Leu|Glu|
| | | |340| | | | |345| | | | |350| |
|Gly|Pro|Phe|Met|Pro|Pro|Arg|Met|Lys|Met|Asp|Arg|Asp|Pro|Leu|Gly|
| | | |355| | | | |360| | | | |365| |
|Gly|Leu|Arg|Asp|Met|Phe|Gly|Gln|Met|Pro|Gly|Ser|Gly|Ile|Gly|Thr|
| | |370| | | |375| | | | |380| | | |
|Gly|Pro|Gly|Val|Ile|Gln|Asp|Thr|Phe|Ser|Pro|Thr|Met|Gly|Arg|His|
|385| | | | |390| | | | |395| | | | |400|
|Arg|Ser|Asn|Gln|Leu|Phe|Asn|Gly|His|Gly|Gly|His|Ile|Met|Pro|Pro|
| | | | |405| | | | |410| | | | |415| |
|Thr|Gln|Ser|Gln|Phe|Gly|Glu|Met|Gly|Gly|Lys|Phe|Met|Lys|Ser|Gln|
| | | |420| | | | |425| | | | |430| | |
|Gly|Leu|Ser|Gln|Leu|Tyr|His|Asn|Gln|Ser|Gln|Gly|Leu|Leu|Ser|Gln|
| | |435| | | | |440| | | | |445| | | |
|Leu|Gln|Gly|Gln|Ser|Lys|Asp|Met|Pro|Pro|Arg|Phe|Ser|Lys|Lys|Gly|
| | |450| | | | |455| | | | |460| | | |
|Gln|Leu|Asn|Ala|Asp|Glu|Ile|Ser|Leu|Arg|Pro|Ala|Gln|Ser|Phe|Leu|
|465| | | | |470| | | | |475| | | | |480|
|Met|Asn|Lys|Asn|Gln|Val|Pro|Lys|Leu|Gln|Pro|Gln|Ile|Thr|Met|Ile|
| | | | |485| | | | |490| | | | |495| |
|Pro|Pro|Ser|Ala|Gln|Pro|Pro|Arg|Thr|Gln|Thr|Pro|Pro|Leu|Gly|Gln|
| | | |500| | | | |505| | | | |510| | |
|Thr|Pro|Gln|Leu|Gly|Leu|Lys|Thr|Asn|Pro|Pro|Leu|Ile|Gln|Glu|Lys|
| | |515| | | | |520| | | | |525| | | |
|Pro|Ala|Lys|Thr|Ser|Lys|Lys|Gln|Pro|Pro|Ser|Lys|Glu|Glu|Leu|Leu|
| |530| | | | |535| | | | |540| | | | |
|Lys|Leu|Thr|Glu|Ala|Val|Val|Thr|Asp|Tyr|Leu|Asn|Ser|Gly|Asn|Ala|
|545| | | | |550| | | | |555| | | | |560|
|Asn|Glu|Ala|Val|Ser|Gly|Val|Arg|Glu|Met|Arg|Ala|Pro|Lys|His|Phe|
| | | | |565| | | | |570| | | | |575| |
|Leu|Pro|Glu|Met|Leu|Ser|Lys|Val|Ile|Ile|Leu|Ser|Leu|Asp|Arg|Ser|
| | | |580| | | | |585| | | | |590| | |
|Asp|Glu|Asp|Lys|Glu|Lys|Ala|Ser|Ser|Leu|Ile|Ser|Leu|Leu|Lys|Gln|
| | |595| | | | |600| | | | |605| | | |
|Glu|Ala|Ile|Ala|Thr|Ser|Asp|Asn|Phe|Met|Gln|Ala|Phe|Leu|Asn|Val|
| |610| | | | |615| | | | |620| | | | |
|Leu|Glu|Gln|Cys|Pro|Lys|Leu|Glu|Val|Asp|Ile|Pro|Leu|Val|Lys|Ser|
|625| | | | |630| | | | |635| | | | |640|
|Tyr|Leu|Ala|Gln|Phe|Ala|Ala|Arg|Ala|Ile|Ile|Ser|Glu|Leu|Val|Ser|
| | | |645| | | | |650| | | | |655| | |
|Ile|Ser|Glu|Leu|Ala|Gln|Pro|Leu|Glu|Ser|Gly|Thr|His|Phe|Pro|Leu|
| | |660| | | | |665| | | | |670| | | |
|Phe|Leu|Leu|Cys|Leu|Gln|Gln|Leu|Ala|Lys|Leu|Gln|Asp|Arg|Glu|Trp|
| | |675| | | | |680| | | | |685| | | |
|Leu|Thr|Glu|Leu|Phe|Gln|Gln|Ser|Lys|Val|Asn|Met|Gln|Lys|Met|Leu|

```
              690                          695                       700
Pro   Glu   Ile   Asp   Gln   Asn   Lys   Asp   Arg   Met   Leu   Glu   Ile   Leu   Glu   Gly
705                           710                     715                                 720

Lys   Gly   Leu   Ser   Phe   Leu   Phe   Pro   Leu   Leu   Lys   Leu   Glu   Lys   Glu   Leu
                        725                     730                           735

Leu   Lys   Gln   Ile   Lys   Leu   Asp   Pro   Ser   Pro   Gln   Thr   Ile   Tyr   Lys   Trp
                  740                     745                                 750

Ile   Lys   Asp   Asn   Ile   Ser   Pro   Lys   Leu   His   Val   Asp   Lys   Gly   Phe   Val
            755                           760                           765

Asn   Ile   Leu   Met   Thr   Ser   Phe   Leu   Gln   Tyr   Ile   Ser   Ser   Glu   Val   Ser
      770                           775                           780

Pro   Pro   Ser   Asp   Glu   Thr   Asp   Ser   Ser   Ser   Ala   Pro   Ser   Lys   Glu   Gln
785                           790                           795                           800

Leu   Glu   Gln   Glu   Lys   Gln   Leu   Leu   Leu   Ser   Phe   Lys   Pro   Val   Met   Gln
                  805                           810                           815

Lys   Phe   Leu   His   Asp   His   Val   Asp   Leu   Gln   Val   Ser   Ala   Leu   Tyr   Ala
                  820                     825                           830

Phe   Gln   Val   His   Cys   Tyr   Asn   Ser   Ser   Phe   Pro   Lys   Gly   Met   Leu   Leu
            835                           840                           845

Arg   Phe   Phe   Val   His   Phe   Tyr   Asp   Met   Glu   Ile   Ile   Glu   Glu   Glu   Ala
850                           855                           860

Phe   Leu   Ala   Trp   Lys   Glu   Asp   Ile   Thr   Gln   Glu   Phe   Pro   Gly   Lys   Gly
865                     870                           875                                 880

Lys   Ala   Leu   Phe   Gln   Val   Asn   Gln   Trp   Leu   Thr   Trp   Leu   Glu   Thr   Ala
                  885                           890                           895

Glu   Glu   Glu   Glu   Ser   Glu   Glu   Glu   Ala   Asp
                  900                           905
```

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TATANTGATC NNNA            14

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TATANTGATC NNNNA          15

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TATANTGATC NNNNNA        16

SCREENING METHODS TO DETECT MRNA TARGETS OF EDITING ENZYMES

FIELD OF THE INVENTION

The present invention relates to RNA editing polypeptides and methods for screening mRNA for editing.

BACKGROUND OF THE INVENTION

Apolipoprotein B occurs naturally in two forms, apo-B100 and apo-B48, both encoded by the same gene. Apo-B100, a 550 KD protein, is the major protein responsible for cholesterol transport in the blood and plays a crucial role in cholesterol and lipoprotein metabolism. Apo-B100 is an integral component of very low density lipoproteins (VLDL) and intermediate density lipoproteins (IDL), and is the sole component of low density lipoprotein (LDL). Apo-B48, a 264 KD protein, is synthesized in the intestines of humans and rabbits and in the liver and intestines of rats and mice. In mice and rats, hepatic-derived apo-B48 is a component of VLDL; the total VLDL is a mixture of VLDL containing apo-B100 or apo-B48. Intestinally derived apo-B48 is secreted as an integral component of chylomicrons.

Apo-B48 is produced by a biological process in which the apoB primary transcript is postranslationally modified by a type of RNA processing known as RNA editing. The term RNA editing is used to describe the specific modification of mRNA (or the coding region of pre-RNA) that alters the genetic information encoded in the transcript.

Apolipoprotein B mRNA editing deaminates a specific cytidine ($C^{6666}$) to create a uridine. This changes the codon at position 2153 from a genomically encoded CAA (glutamine) to an in-frame stop codon (UAA). Apolipoprotein B mRNA editing occurs in the small intestine of all mammals and in the liver of rats, mice, dogs, and horses.

Hepatic apo-B mRNA editing in the rat and mouse, both of which normally modify approximately 65% of the apoB mRNA, is developmentally and hormonally regulated. Editing activity is regulated by growth hormone, thyroxine, cortisol, fasting, and diet. Apolipoprotein B mRNA editing also demonstrates developmental regulation in the human intestine. Human fetal intestine at 11 weeks of gestation predominantly produces apo-B100, whereas at 16 weeks of gestation, both apo-B100 and apo-B48 are secreted in roughly equal proportions. In the adult intestine, only apo-B48 is secreted.

A specific 11 nucleotide "mooring" sequence in apoB mRNA occurring 5 nucleotides downstream from $C^{6666}$ is critical for editing in vitro. When the mooring sequence is inserted into another location on apoB or non-apoB cDNA, the resulting chimeric RNA is edited in vitro (Driscoll et al. *Mol. Cell. Biol.* 13: 7288–7294 (1993); Backus et al. *Biochim. Biophys. Acta.* 1217: 65–73 (1994); Shah et al. *J. Biol. Chem.* 266: 16301–16304 (1991); Backus et al. *Biochim. Biophys. Acta.* 1219: 1–14 (1994)).

Several proteins appear to be necessary for apoB mRNA editing in vitro. One of these proteins has been cloned from a rat intestinal library (Teng et al. *Science* 260: 1816–1819 (1993)). This 27 kD protein, which deaminates cytidine$^{6666}$ in apoB mRNA, has been designated APOBEC-1 (apoB mRNA-editing enzyme catalytic polypeptide #1) (Davidson et al. RNA 1:3 (1995)). The major functional domains of this RNA editing polypeptide are highly conserved in the cloned homologues of rat APOBEC-1 from human (Hadjiagapiou et al. *Nucleic Acids Res.* 22: 1874–1879 (1994); Lau et al. *Proc. Natl. Acad. Sci. U.S.A.* 91: 8522–8526 (1994)), rabbit (Yamanaka et al. *J. Biol. Chem.* 269: 21725–21734 (1994)), and mouse (Nakamuta et al. *J. Biol. Chem.* 270: 13042–13056 (1995)).

Transgenic mice and rabbits expressing APOBEC-1 have been generated (Yamanaka etal. *Proc. Natl. Acad. Sci. U.S.A.* 92: 8483–8487 (1995)). The transgenic mice and rabbits had liver dysplasia, and many developed hepatocellular carcinomas.

Comparison of gene expression in different tissues or under different conditions can be performed using the technique of differential mRNA display (Liang and Pardee, *Science* 257: 967–971 (1992)), also termed differential display reverse transcriptase PCR. In this technique, two or more RNA populations (e.g., RNA preparations from different tissues) are made into cDNA using reverse transcriptase and a set of oligonucleotide primers, one being anchored to the polyadenylate tail of a subset of mRNAs by, for example, the two nucleotide sequence CA, the other being short and arbitrary in sequence so that it anneals at different positions relative to the first primer. The resulting cDNA is amplified by PCR, using a 5' primer of arbitrary base sequence, chosen to anneal at positions randomly distributed in distance from the poly(A) tail. The resulting amplified DNA sequences can be separated by gel electrophosis. An amplified DNA band can be subcloned into a vector, or can be sequenced, for example, by using extended primers for futher amplification (Wang and Feuerstein, *Biotechniques* 18: 448–452 (1995)), ligation linked PCR (Reeves et al. *Biotechniques* 18: 18–20 (1995)).

Recent studies have provided some insight into the genetic basis for obesity. A mouse obesity gene, ob, and its human homologue have been cloned and sequenced (Zhang et al. *Nature* 372: 425–432 (1994)). Mutation in ob results in profound obesity and type II diabetes as part of a syndrome that resembles morbid obesity in humans (Friedman et al. *Genomics* 11: 1054–1062 (1991). Halaas et al. (*Science* 269: 543–546 (1995); Pelleymounter et al. (*Science* 269: 540–543(1995)); and Campfield et al. (*Science* 269: 546–549(1995)) described the weight-reducing effects of the plasma protein OB (leptin) encoded by the obese gene. A transmembrane receptor for OB protein has been cloned (Tartaglia et al. *Cell* 83: 1263 (1995)). Mice with mutations in the diabetes gene db have a phenotype similar to mice having mutations in ob. Chua et al. (*Science* 271: 994–996(1996)) have demonstrated by genetic mapping and genomic analysis, that mouse db, rat fatty (a homologue of db), and the gene encoding OB-R are the same gene.

SUMMARY OF THE INVENTION

The expression of APOBEC-1 in the liver of transgenic mice can cause liver dysplasia and liver tumors, and the expression of human APOBEC-1 in the intestine, stomach, or brain can cause obesity. Promiscuous editing of mRNAs other than apoB is correlated to these these phenotypic changes. The instant invention discloses novel techniques for detecting aberrantly edited mRNAs, and hence, genes responsible for non-wild type phenotypes.

One aspect of the invention is a method for detecting mRNA candidates for editing in a tissue, comprising
 a) generating cDNA from RNA in the tissue using one or more mooring primers and reverse transcriptase;
 b) amplifying the cDNA of step (a) by polymerase chain reaction using one or more mooring primers and one or more 5' arbitrary primers, and
 c) separating the products of step (b) by gel electrophoresis;

wherein the mooring primer comprises a sequence complementary to a sequence having at least 80% sequence homology to a known mooring sequence.

Another aspect of the invention is a method for identifying an obesity gene in an animal, comprising a) generating an obese transgenic animal expressing an exogenous RNA editing polypeptide;

b) generating cDNA from RNA in tissue from obese and control animals using one or more mooring primers and reverse transcriptase;

c) amplifying the cDNA of step (b) by polymerase chain reaction using one or more mooring primers and one or more 5' arbitrary primers;

d) comparing the products of step (c) to identify at least one RNA species differing in occurrence in the obese and control animals;

wherein the mooring primer comprises a sequence complementary to a sequence having at least 80% sequence homology to a known mooring sequence.

Another aspect of the invention is a method for identifying an oncogene in an animal, comprising a) generating a transgenic animal expressing an exogenous RNA editing polypeptide;

b) identifying animals with a non-wild type phenotype;

c) generating cDNA from RNA from a tissue of the animals of step b) and control animals, wherein the tissue expresses the RNA editing polypeptide, using one or more mooring primers and reverse transcriptase;

d) amplifying the cDNA of step (c) by polymerase chain reaction using one or more mooring primers and one or more 5' arbitrary primers;

e) comparing the products of step (d) to identify at least one RNA species differing in occurrence in the non-wild type and control animals;

wherein the mooring primer comprises a sequence complementary to a sequence having at least 80% sequence homology to a known mooring sequence.

Another aspect of the invention is a method for screening for aberrantly edited mRNA, comprising:

(a) identifying a DNA sequence in a data bank, wherein the DNA sequence contains a mooring-like sequence;

(b) preparing cDNA from mRNA in a tissue of interest with a non-wild type phenotype and from the tissue of interest with a wild type phenotype;

(c) amplifying the cDNAs from step (b) by polymerase chain reaction using a 5' primer specific for the DNA sequence of step (a) and a 3' mooring sequence primer, wherein the mooring sequence primer comprises a sequence complementary to a sequence having at least 80% sequence homology to a known mooring sequence;

(d) comparing the products of step (c) to identify aberrantly edited mRNA in the tissue having a non-wild type phenotype.

Another aspect of the invention is a sequence for use as a primer comprising in the 5' to 3' direction a sequence complementary to a mooring-like sequence; 3 to 5 degenerate nucleotides; and adenosine.

Another aspect of the invention is a composition comprising a nucleic acid encoding NTA1, an obesity-related protein. Other aspects of the invention include a composition comprising purified NTA1.

BRIEF DESCRIPTION OF THE DRAWINGS

FIG. 5 comprises FIGS. 5A–C and is a diagram depicting the nucleotide sequence encoding NTA1 and the predicted amino acid sequence of NTA1. (SEQ ID NO: 8)

DESCRIPTION OF THE PREFERRED EMBODIMENTS

General Methods

Figures 1, 3:
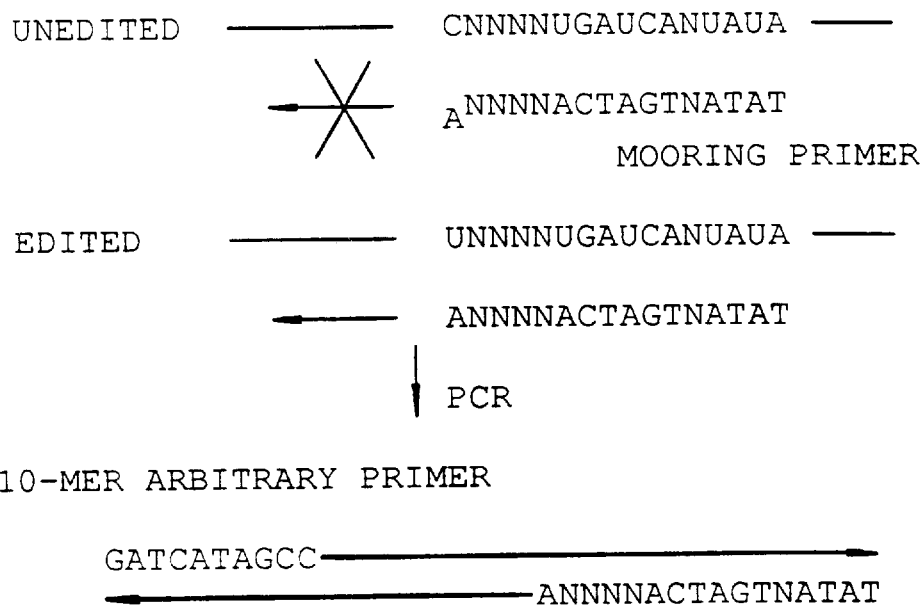
FIG. 1 is a diagram depicting the use of mooring-dependent polymerase chain reaction (PCR) to identify edited mRNA. (SEQ ID NO'S 2–5)
FIG. 3 is a diagram depicting editing of multiple cytidines in NTA1 mRNA from APOBEC-1 transgenic mouse liver. Arrows indicate edited cytidines. (SEQ ID NO'S 6, 7)

In some embodiments of the instant invention methods are provided for the identification of mRNAs that are candidates for RNA editing by virtue of having a mooring or mooring-like sequence, for screening candidate mRNAs for aberrant editing, and for identifying genes encoding such candidate mRNAs.

To identify mRNA candidates for RNA editing, total RNA is first isolated from a cell culture or tissue of interest by a variety of methods well known in the art (see, for example, Sambrook, et. al. *Molecular Cloning.* Cold Spring Harbor Laboratory, Cold Spring Harbor, N.Y. (1989)). To selectively enrich the cDNA population for mRNAs that are likely to be subjected to editing, cDNA is generated by using "mooring primers" as primers for reverse transcriptase. These "mooring primers" are sequences complementary to known "mooring sequences" or "mooring-like sequences." As used herein, the term "mooring sequence" is intended to refer to a nucleotide sequence correlated with editing of an mRNA. An example of a mooring sequence is the specific 11 nucleotide "mooring" sequence 5'-UGAUCANUAUA[SEQ ID NO:1]-3 in apo-B mRNA occurring 5 nucleotides downstream from $C^{6666}$. A "mooring-like" sequence is a sequence having greater than 80% homology with a mooring sequence.

Such mooring primers can be about 10 to about 20 nucleotides in length, more preferably about 13 to about 16 nucleotides in length. One or more mooring primers can be used in the generation of cDNA. Typically, to identify mRNAs that are candidates for editing, sets of mooring primers will be synthesized having desired sequences by techniques well known in the art for oligonucleotide synthesis (See, for example, Gait, ed. *Oligonucleotide Synthesis. A Practical Approach.* IRL Press, N.Y. (1984)).

In some embodiments of the invention, mRNAs that have been aberrantly edited can be identified by designing the mooring primers to include a sequence complementary to a mooring sequence or mooring-like sequence, followed by 3–5 nucleotides, and an adenosine at the 3' end. Preferably, the 3–5 nucleotides are degenerate. The C-terminal adenosine allows more efficient amplification of edited mRNA containing thymidine than the unedited mRNA containing cytidine. In other embodiments of the invention, a cytosine, thymidine, or guanosine residue is preferable as the 3' terminal residue, depending on the change introduced into mRNA by the RNA editing polypeptide. In further embodiments of the invention, the mooring primer has the general formula

5'-TATANTGATCXA-3' (SEQ ID NOS: 10–12)

wherein N is any nucleotide and X is 3 to 5 nucleotides. Preferably, X is degenerate.

Conditions for cDNA generation from RNA using reverse transcriptase are well known in the art. See for example, Liang et. al. *Science* 257: 967–971 (1991).

To amplify the cDNA generated with mooring primers, the mooring primers are additionally used as 3' primers in PCR amplification. The 5' primers are typically different sets of arbitrary primers chosen such that annealing positions to cDNA are randomly distributed from the mooring sequence. Typically, such 5' primers are designed to anneal to the cDNA at a position less than 2 to 3 KB from the mooring or mooring-like sequence. Preferably, the position is less than about 500 nucleotides from the mooring or mooring-like sequence to allow better resolution on a sequencing gel. The 5' primer is preferably relatively short, from about 8 nucleotides to 20 nucleotides. Examples of arbitrary sequences include 5'-GATCATAGCC[SEQ ID NO: 2]-3'.

Preferably, the PCR is performed with radiolabeled nucleotides to allow detection by autoradiography. Conditions for PCR are well known in the art. See, for example, Liang et. al., supra.

The resulting amplified DNA sequences can be separated by gel electrophosis by techniques well known in the art (see, for example, Liang et. al., supra). An amplified DNA band can be subcloned into a vector, or can be sequenced, for example, by using extended primers for futher amplification (Wang and Feuerstein, *Biotechniques* 18: 448–452 (1995)), or ligation linked PCR (Reeves et al. *Biotechniques* 18: 18–20 (1995)).

Searches of databases, such as Genbank, can also be used in the identification of candidate mRNAs for editing. As shown in the examples below, several editing candidates were obtained by searching a database for sequences similar to the mooring sequence of ApoB. Once identified, as exemplified below, specific primers can be designed to amplify only the sequence of interest by PCR.

In some embodiments of the invention, it is desirable to determine whether an mRNA candidate for RNA editing can be edited by an editing polypeptide such as APOBEC-1. This can be accomplished in vitro, for example, by adding recombinant APOBEC-1, a tissue extract containing other components of the editing enzyme complex and a substrate synthetic RNA having a desired sequence and analyzing the RNA for editing as described above. For examples of in vitro editing assays, see Backus, et. al. *Biochim. Biophys. Acta.* 1217: 65–73 (1994) and Giannoni, et. al. *J. Biol. Chem.* 269: 5932–5936 (1994). In further embodiments of the invention, variants of an RNA of interest, created by substitutions in the DNA template, can be subjected to such an in vitro assay to determine what sequences are involved in the editing process.

In a further embodiment of the invention, a transgenic animal can be provided expressing an exogenous RNA editing polypeptide, such as APOBEC-1, as exemplified below. In such animals, in vivo editing of a candidate mRNA by APOBEC-1 in a tissue of interest can be determined as described above, begining with preparing RNA from the tissue. In some embodiments of the invention, it can be advantageous to provide a transgenic animal having multiple copies of an RNA editing enzyme. Such multiple copies can lead to higher levels of expressison of the editing enzyme, thereby resulting in aberrant editing of a candidate mRNA.

Transgenic animals can be generated by techniques well known in the art. See, for example, U.S. Pat. No. 4,736,866.

In additional embodiments of the invention, the generation of a transgenic animal can result in a non-wild type phenotype. For example, the experimental results below demonstrate the generation of obese APOBEC-1 transgenic animals and APOBEC-1 animals with pathological liver changes. In such instances, it is desirable to identify mRNAs that have been edited in those tissues by the RNA editing polypeptide. Aberrant editing of an mRNA by an RNA editing polypeptide in a cell culture, tissue or animal possessing pathological or non-wild type phenotype provides an opportunity to identify genes involved in the generation of those phenotypes. Without being limited to any one theory, such aberrant editing could result from the presence of an editing polypeptide not normally expressed in the tissue, by an excess of such a polypeptide, by an excess of such a polypeptide normally found in the tissue, and so on. The identification of such mRNAs thus provides insight into the role of the genes, including oncogenes and obesity modifying genes, encoding them in growth, differentiation, or lipid accumulation, and into the possible role of an RNA editing enzyme or polypeptide in causing obesity or as an oncogene. The term "oncogene" as used herein is intended to include cancer genes, transforming genes, and genetic loci responsible for neoplastic changes in the host cell. "Obesity gene" as used herein is intended to include obesity modifying genes encoding products acting on adipose tissues or on distant sites controlling lipid metabolism and accumulation.

In such transgenic animals, the use of mooring primers for cDNA generation and PCR, along with arbitrary 5' primers for PCR allows the identification of candidate mRNA for editing. Preferably, the use of mooring primers having 3 to 5 degenerate nucleotides plus adenosine following the mooring or mooring like complementary sequence described above allows the identification of mRNA likely to have experienced a C to U change. More preferably, an RNA preparation from the non-wild type tissue is compared with tissue having a wild type phenotype to identify those mRNAs which have been edited aberrantly. Control animals providing such a wild type phenotype can include transgenic animals, transgenic animals generated with innocuous or unrelated transgenes, or non-transgenic animals. Sequencing of the PCR products, either directly or after cloning, provides a basis for isolating the gene of interest from a library. The sequencing information also provides opportunities to search databases for sequences related to the PCR product.

Once such an edited mRNA is identified, and the sequence of the corresponding cDNA obtained, the amino acid sequence of the polypeptide product of that cDNA can be predicted. Such polypeptides can be synthesized, obtained by expression techniques well known in the art, or isolated from a tissue of interest. Such polypeptides can be useful as therapeutic reagents in situations wherein the edited version of the polypeptide results in a pathological state. Therapeutic use of the non-edited version, or a fragment of the polypeptide having biological function of the non-edited version, can restore, ameliorate, or at least partly reduce the severity of the pathological state. Additionally, such polypeptides or the edited version (i.e. the product of the edited mRNA) thereof can be used in the preparation of antibodies for therapeutic use in a pathological condition and as research tools for investigating the role of the protein in such processes as growth and development.

The scope of the invention is intended to include nucleic acid which is homologous to NTA1 nucleic acid, including edited versions, and polypeptides, including the products of edited verions of mRNA, which are homologous to NTA1 polypeptide. Generally, this will be about 90% and is more typically about 95%.

Experimental Examples

I. APOBEC-1 Transgenic Mice with Transformed Phenotype

In this study, transgenic rabbits and mice expressing rabbit APOBEC-1 in their livers were generated to determine if the hepatic expression of APOBEC-1 would lower LDL concentrations by reducing apo-B100 synthesis by the liver.

To generate the transgenic mice and rabbits, a full-length rabbit APOBEC-1 cDNA was subcloned into a vector, (pLiv11) containing a promoter, an intron, and a hepatic control region, all from the human apo-E gene. Other heterologous cDNAs previously cloned into this vector were expressed robustly and predominantly in the liver (Fan et al. *Proc. Natl. Acad. Sci. U.S.A.* 91: 8724–8728 (1994)). Specifically, a cDNA fragment of rabbit APOBEC-1 was isolated from the plasmid pREPR (Yamanaka etal. *J. Biol Chem.* 269: 21725–21734 (1994)) by digestion with EcoRI and subcloned into pLiv11, which had been linearized with Mun I, to produce the vector pLivREPR. A SalI-SpeI fragment of pLivREPR was gel-purified by Qiaex (Qiagen, Chatsworth, Calif.) and microinjected into fertilized oocytes of strain ICR mice (Charles River Breeding Laboratories) and New Zealand White rabbits. Founder pups were identified by Southern blot analysis of genomic DNA from mouse tails or rabbit ears with a $^{32}$P-labeled probe of rabbit APOBEC-1 cDNA. The transgene copy number was estimated by using endogenous rabbit APOBEC-1 as a control. Four independent trangenic mouse lines (I-20, I-22, I-28L, and I-28H) were established from the three mouse founders expressing wild-type rabbit APOBEC-1, and their transgene numbers were estimated to be 7, 17, 3, and 10, respectively.

transgenic mice. The apparent lack of apo-B100 in the transgenic mouse lipoprotein was confirmed by SDS/PAGE.

Unexpectedly, all of the transgenic mice and a transgenic rabbit displayed liver dysplasia, and many transgenic mice developed hepatocellular carcinomas. The livers of the transgenic mice were at least twice as large, and in some cases, 10 times as larger than those of their non-transgenic litter mates. One liver weighed 18 g, which was 40% of the entire weight of the mouse. Histological examination of the livers revealed that hepatocytes were dysplastic, exhibiting variations in nuclear and cellular morphology concomittant with changes in the cytoplasm-to-nucleus ratio. In all of the mouse lines, large multinodular tumors, having the morphological appearance of hepatocellualr carcinomas, were observed. One transgenic mouse had severe hepatic hyperplasia, with nodules of trabecular carcinoma, but only minimal lipid deposits at 24 days.

The transgenic rabbit with 17 copies of the transgene appeared normal at birth but grew more slowly than its nontransgenic litter mates. After 8 weeks it became weak and immobile and, therefore, was euthanized. The transgenic rabbit's weight was about 50% of that of its litter mate (1160 vs. 2250 g). Necropsy revealed an enlarged liver, weighing about 1.5 times more than that of its nontransgenic littermate (112 vs. 72 g). The transgenic rabbit's liver had visible scarring, fibrosis, and cytoplasmic lipid droplets. In the transgenic rabbit founder, as in the mice, APOBEC-1 mRNA was expressed mainly in the liver. Primer extension analysis showed that 78% of the apo-B mRNA was edited in

TABLE 1

Pathology of Transgenic Mouse Livers

| Mouse lines | Mice studied no. | Gene copy no. | Age at analysis, days | Liver/body weight ratios, % (n) | Mice with pathology, no. | | |
|---|---|---|---|---|---|---|---|
| | | | | | Normal-minimal dysplasia | Dysplasia with fatty change | Hepatocellular carcinoma |
| Transgenic (wild-type) | | | | | | | |
| 1–20 | 21 | 7 | 76–274 | 12.0(16) | 0 | 20 | 1 |
| 1–22 | 5 | 17 | 92–200 | 13.3 (1) | 0 | 3 | 2 |
| 1–28H | 5 | 10 | 29–121 | 23.2 (3) | 0 | 1 | 4 |
| 1–28L | 4 | 3 | 66–209 | 21.4 (1) | 1 | 2 | 1 |
| Transgenic (mutant) | 8 | | 257–401 | 4.8 (4) | 8 | 0 | 0 |
| Control | 20 | | 66–140 | 5.5(19) | 20 | 0 | 0 |

One transgenic rabbit founder had one copy of the transgene, and the other founder had 17 copies.

In the transgenic animals, the transgene APOBEC-1 mRNA was expressed predominantly in the liver. The apoB mRNAs from the livers of the transgenic mice and rabbits were extensively edited, and the transgenic animals had reduced concentrations of apo-B100 and LDL compared to those of the control animals. Specifically, an average of 92% of apo-B mRNA was edited in the livers of all four transgenic mouse lines (n=26). In the transgenic control mouse line, no increase in the amount of edited apoB mRNA (82%, n=4) was observed over that of the non-transgenic mouse line (83%, n=23). Liver extracts from wild-type APOBEC-1 transgenic mice were 15 fold more active in editing a synthetic apoB RNA substrate in vitro than liver extracts from age- and sex-matched control mice. This finding demonstrated that APOBEC-1 was overexpressed, resulting in excess editing activity in the transgenic mouse livers. As expected by agarose gel elctrophoroesis, B-migrating lipoproteins (LDL) were not detected in the plasma of the the transgenic rabbit liver, whereas no significant editing of apo-B mRNA occurred in the control rabbit liver. Although fasted plasma from normal rabbit contains only apo-B100, the lipoproteins isolated from the high copy number transgene rabbit contained greater than 50% apo-B48.

To determine whether the mechanism for dysplasia in the APOBEC-1 transgenic animals is the aberrant editing of other mRNAs, other hepatic mRNAs with mooring sequence motifs similar to that of apo-B mRNA were examined for this type of editing (i.e., cytidine deamination). GenBank was searched for sequences similar to the mooring sequence using the FASTA program (Pearson et al. *Proc. Natl. Acad. Sci. U.S.A.* 85: 2444–2448 (1988)). Twenty three rodent sequences were found to have the exact mooring sequence. Among these are the mouse fatty acid synthase (FAS) and mouse P1 protein (P1), both of which contain a cytidine residue 4–6 nucleotides upstream from the mooring sequence. Furthermore, greater than 100 sequences were identified with sequence motifs just 1 nucleotide different from the mooring sequence. These include mouse protein-tyrosine kinase TEC and mouse prostaglandin synthase (TIS10), which contain a cytidine residue 5 or 7 nucleotides upstream from the mooring sequences, respectively.

To determine whether these mRNA were edited in vivo, RNAs isolated from control and transgenic mouse livers were amplified by reverse transcription-PCR. The PCR products were analyzed for editing by primer-extension anlaysis. None of the four mRNAs (P1, FAS, TIS10, TEC) were edited in the livers of the control mice. Without being limited to any one theory, this result suggests that the mooring sequence is normally not sufficient to support editing. Even in transgenic mice with high hepatic editing levels, three of the transcripts were not edited. However, mouse protein-tyrosine kinase TEC was edited in transgenic mice, providing a second example of C to U editing of an mRNA. This particular change was a silent codon change, and thus could not be the cause of the observed pathological phenotype. Nevertheless, these results establish that other cytidines in mammalian mRNA can be the targets of APOBEC-1 mediated deamination. Specific C to U changes can result in the formation of new termination codons, new initiation codons, and missense mutations, all of which can have potentially severe biological consequnces.

Although apoB mRNA editing does not normally modify DNA, it is possible that the overexpressed APOBEC-1 might modify small amounts of DNA. However, $C^{6666}$ in a 282 bp apoB DNA fragment, 6504–6785, was not edited in vitro. Moreover, PCR and primer extension analysis of genomic apoB DNA from transgenic mouse livers overexpressing APOBEC-1 indicated that the genomic $C^{6666}$ was not edited in vivo. It is thus likely that the predisposition to hepatocellular carcinoma is not due to DNA modifications.

2. APOBEC-1 Transgenic Mice with Obese Phenotype

A second transgenic animal model was generated by using human genomic DNA containing APOBEC-1. These mice were generated using the APOBEC-1 promoter, rather than that of apo-E, which was used in the construct above. Five transgenic mouse lines were generated using the procedure described above that had from two to seven copies of the human APOBEC-1 transgene. These mice expressed human APOBEC-1 in their intestine, stomach, and brain. The expression of APOBEC-1 in these tissues, with the exception of the brain, mimicked the expression of APOBEC-1 in human tissue.

In four of five lines, 47% of the transgenic mice were obese (at least 10% greater body weight than their nontransgenic littermates). The weights of these mice were from 33% to 54% greater than their nontransgenic littermates. Autopsy examination of the transgenic mice revealed large amounts of abdominal fat compared to the nontransgenic littermate controls. For example, one transgenic mouse contained about 9 grams of abdominal fat compared to about 3 grams in the control animal.

An additional independent control has been generated in the form of an "apo-B48-only" mouse by other investigators at the Gladstone Institutes. Gene targeting in embryonic stem cells has been used to generate mice synthesizing only apo-B48. These non-obese mice are homozygous for the C→T mutation at position 6666 of apo-B cDNA that corresponds exactly to the C→U editing change mediated by APOBEC-1. These mice synthesize only apo-B48 and no apo-B100 and develop normally with livers of normal size, morphology, and function. The histology of the livers of six "apo-B48-only" mice (aged 5–9 months) was examined. Their livers were normal or near-normal and did not have the changes present in the livers of transgenic mice expressing APOBEC-1. The plasma activities of the liver enzyme glutamic-oxaloacetic transaminase (GOT), in international units per liter, were 306±127 (n=4), 91±12 (n=4), 53±6 (n=4), and 98±34 (n=4) for transgenic mice, nontransgenic mice, transgenic mice with the mutant APOBEC-1 construct, and "apo-B48-only" mice, respectively. The glutamic-pyruvic transaminase (GPT) activities were 330±106 (n=4), 26±2 (n=4), 22±2 (n=4), and 29±3 (n=4), respectively.

Thus, the evidence indicated that the tumorigenesis or obesity in the transgenic mice expressing APOBEC-1 was caused by the promiscuous editing of other mRNAs involved in cell functions or, in the case of obesity, an mRNA involved in either the endocrine, metabolic, or behavioral control of energy metabolism.

3. Screening Technique for Aberrantly Edited mRNAs

The instant invention discloses a novel approach to search for these aberrantly edited mRNAs. This approach, "mooring-dependent PCR," is designed to amplify edited mRNAs selectively. The sequence specificity of apo-B mRNA editing appears to be provided by an 11-nucleotide (nt) sequence motif, the mooring sequence, which is located 5 nt downstream from the cytidine to be edited. Primers (mooring primers) were designed consisting of a sequence complementary to the mooring sequence, followed by 3–5 degenerate nucleotides, and an adenosine at the 3' end (FIG. 1). Because of this adenosine, the mooring primers allow more efficient amplification of edited mRNA containing thymidine than the unedited mRNA containing cytidine. The mooring primers were used as primers for reverse transcriptase in the generation of cDNA and additionally as primers in PCR amplification. The 5' primers were different sets of arbitrary primers chosen such that annealing positions to cDNA were randomly distributed from the mooring sequence.

Figure 2:
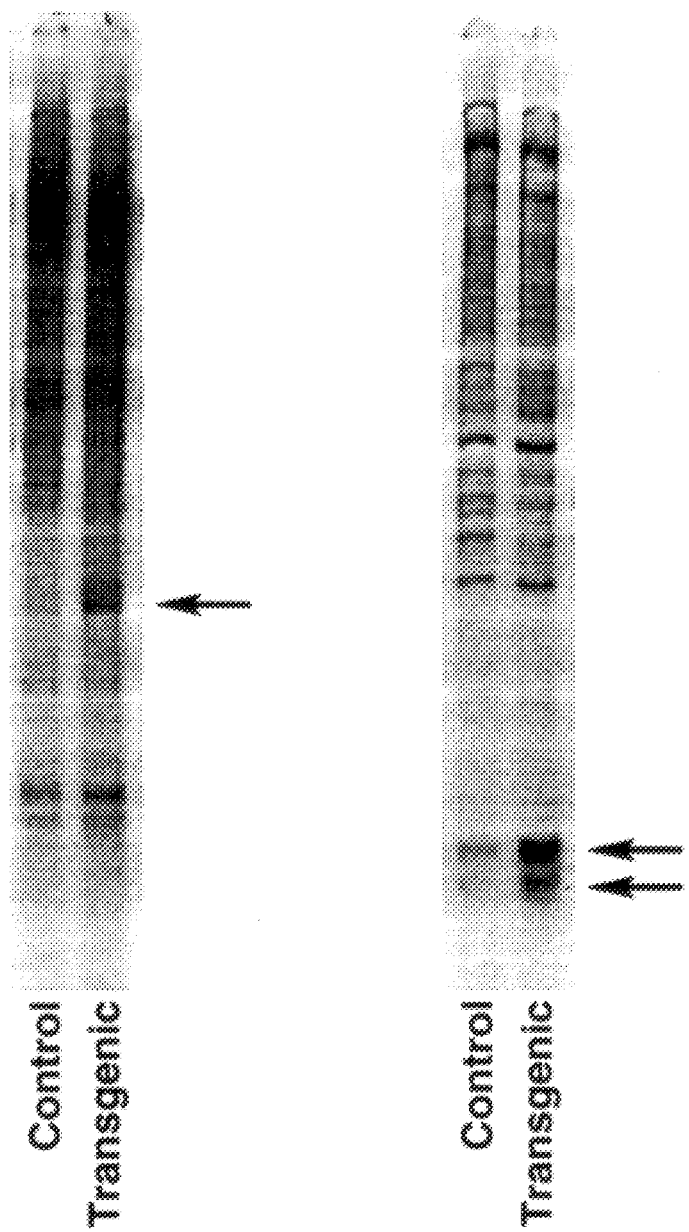
FIG. 2 is an autoradiagram of mooring-dependant PCR amplification products from APOBEC-1 transgenic mouse liver having a higher abundance than in control mice.

Total RNA from control and transgenic mouse livers was isolated and subjected to mooring-dependent PCR. The PCR was performed in the presence of radioactive deoxynucleotides, and the radioactive amplification products were separated on a DNA-sequencing gel. Shown in FIG. 2 are two examples of an amplification product from the transgenic mouse liver having a higher abundance than that of the control mice. These bands were excised from the gel, and the DNAs were reamplified by mooring-dependent PCR and sequenced.

4. Identification of a Novel Target of APOBEC-1 #1 (NTA1)

Figure 4:
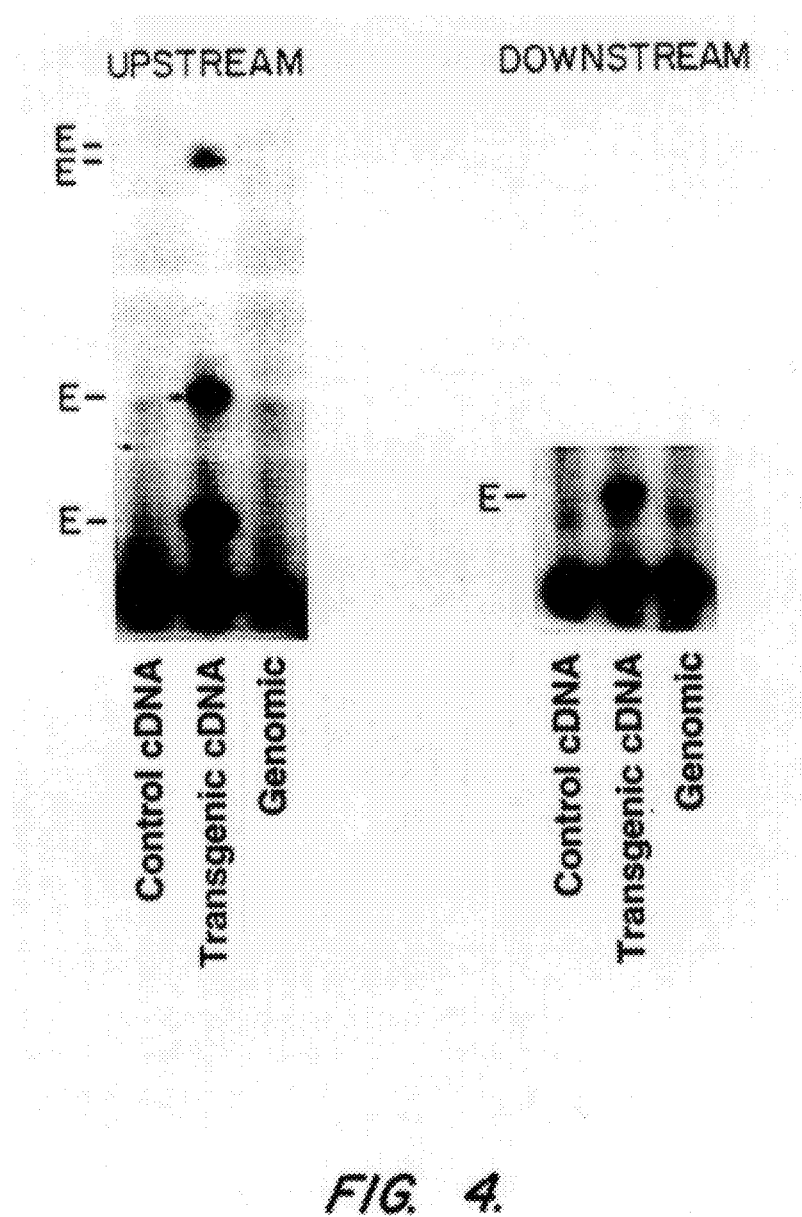
FIG. 4 is an autoradiagram depicting primer extension analysis of PCR amplified APOBEC-1 transgenic mouse liver. "E" denotes edited mRNA.

Initial studies using mooring-dependent PCR have identified six differentially amplified bands. A search of Genbank revealed that one of these six clones was nearly identical to several human-expressed sequence tags (ESTs). ESTs are partial cDNA sequences that have not been characterized. Importantly, the mouse sequence had thymidines in place of several cytidines in the human sequence, suggesting that these cytidines may be edited in the APOBEC-1 transgenic mice. To confirm this editing, primers were designed, based on the human sequence, and used to amplify the sequence from control mouse liver RNA, transgenic mouse liver RNA, and mouse genomic DNA. The cDNA generated from the control mouse liver mRNA and genomic DNA had the same sequence as that of the human. In contrast, the cDNA generated from the APOBEC-1 transgenic mouse liver mRNA had thymidines in the place of several cytidines, as observed in the cDNA from differential display, demonstrating that these cytidines are edited only in the transgenic mice (FIG. 3). Primer extension analysis has further confirmed that approximately 20% of each cytidine is edited in the transgenic mice (FIG. 4). This mRNA has the laboratory designation of "NTA1," an acronym for novel target of APOBEC-1 #1. The APOBEC-1 transgenic rabbit founder described above that developed severe hepatic dysplasia was determined to also have edited NTA1.

Five EST clones of NTA1 were obtained from the Washington University-Merck EST project. Sequencing of the longest clone (2.4 kb) revealed a single open reading frame of 1,626 base pairs and a relatively long 3' untranslated region (UTR) of 758 base pairs. Apparently, this clone is not full-length. Northern blot analysis indicated that the transcript is about 4 kb, and the open reading frame lacks the ATG codon in the Kozak consensus motif for the initiation codon.

5' rapid amplification of cDNA ends (RACE)-PCR was performed to obtain a full-length cDNA clone of NTA1. The nucleotide sequence and predicted amino acid sequence of NT1 are provided in FIGS. 5A–C.

The results indicated that human and mouse sequences are highly conserved and have 95% identity throughout the entire sequence, including the 3' UTR. The last 200 base pairs in the 3' end are nearly identical in the human, mouse, rabbit, and rat. This indicated that this region in 3' UTR may have important functions, such as regulation of stability and/or translation of the NTA1 mRNA. It is in this 3' end region where APOBEC-1 modifies multiple cytidines in the transgenic mouse liver.

Thus, the experimental examples indicate that it is possible to identify mRNAs edited by APOBEC-1 and to determine which one(s) cause cellular transformation and obesity. The mooring-dependent PCR approach of disclosed herein identifies other targets of apo-B mRNA editing. By this strategy, mRNAs aberrantly edited in transgenic organs or other tissues can be detected. This screening technique thus allows both the identification of genes correlated with a particular phenotype and insight into the mechanism of gene function and pathogenesis. Additionally, the APOBEC-1 transgenic mouse provides a novel model for the study of obesity and the identification of genes and gene products related to obesity.

All references cited herein are expressly incorporated by reference in their entirety.

What is claimed is:

1. A method for detecting edited candidate mRNA in a tissue, comprising
   a) generating cDNA from RNA in the tissue using one or more mooring primers and reverse transcriptase;
   b) amplifying the cDNA of step (a) by polymerase chain reaction using one or more mooring primers and one or more 5' arbitrary primers, and
   c) separating the products of step (b) by gel electrophoresis;
      wherein the mooring primer comprises a nucleic acid having the sequence 5'-TATANTGATCAXA-3' wherein X is 3 to 5 nucleotides.

2. The method of claim 1, further comprising
   (d) sequencing one or more products of step (c).

3. The method of claim 1, wherein the tissue is liver.

4. The method of claim 1, wherein the tissue is kidney.

5. The method of claim 1, wherein the tissue is small intestine.

6. The method of claim 1, wherein the arbitrary primer comprises the sequence
   5'-GATCATAGCC-3'.

7. The method of claim 1, wherein one or more products of step (c) are cloned.

8. The method of claim 1, wherein DNA encoding a product of step (c) is isolated from a DNA library.

9. A sequence for use as a primer comprising 5'-TATANTGATCAXA3' wherein X is 3 to 5 nucleotides.

* * * * *

UNITED STATES PATENT AND TRADEMARK OFFICE
CERTIFICATE OF CORRECTION

PATENT NO. : 5,866,333
DATED : February 2, 1999
INVENTOR(S) : Thomas L. Innerarity, et. al.

It is certified that error appears in the above-identified patent and that said Letters Patent is hereby corrected as shown below:

Column 1, line 6, insert the follows:

This invention was made with government support under Grant No. HL47660 awarded by the National Institutes of Health. The Government has certain rights in this invention.

Signed and Sealed this

Twenty-fourth Day of October, 2000

Attest:

Q. TODD DICKINSON

*Attesting Officer*  *Director of Patents and Trademarks*